US008596263B2

(12) United States Patent
    Piper

(10) Patent No.: US 8,596,263 B2
(45) Date of Patent: Dec. 3, 2013

(54) INHALATION ACTUATED NEBULIZER WITH IMPINGEMENT SHIELD

(76) Inventor: Samuel David Piper, Carmichael, CA (US)

( * ) Notice: Subject to any disclaimer, the term of this patent is extended or adjusted under 35 U.S.C. 154(b) by 342 days.

(21) Appl. No.: 12/927,332

(22) Filed: Nov. 12, 2010

(65) Prior Publication Data

US 2011/0114090 A1    May 19, 2011

Related U.S. Application Data

(60) Provisional application No. 61/281,402, filed on Nov. 16, 2009.

(51) Int. Cl.
    *B05B 1/26*  (2006.01)
    *A61M 11/00* (2006.01)

(52) U.S. Cl.
    USPC ............. 128/200.18; 128/200.21; 128/200.14

(58) Field of Classification Search
    USPC ............. 128/200.11–200.22, 200.24, 203.12, 128/203.15, 203.16
    See application file for complete search history.

(56) References Cited

U.S. PATENT DOCUMENTS

| | | | |
|---|---|---|---|
| 3,097,645 A | | 7/1963 | Lester |
| 3,762,409 A * | 10/1973 | Lester ...................... 128/200.14 |
| 4,510,929 A | | 4/1985 | Bordoni |
| 4,588,129 A * | 5/1986 | Shanks .......................... 239/338 |
| 4,741,331 A | | 5/1988 | Wunderlich |
| 5,054,477 A * | 10/1991 | Terada et al. ............. 128/200.14 |
| 5,235,969 A * | 8/1993 | Bellm ...................... 128/200.18 |
| 5,287,847 A * | 2/1994 | Piper et al. ............... 128/200.21 |
| 5,479,920 A | | 1/1996 | Piper |
| 5,503,139 A * | 4/1996 | McMahon et al. ........ 128/200.18 |
| 5,584,285 A | | 12/1996 | Salter |
| 5,687,912 A | | 11/1997 | Denyer |
| 6,116,233 A * | 9/2000 | Denyer et al. ............. 128/200.18 |
| 6,131,568 A * | 10/2000 | Denyer et al. ............. 128/200.21 |
| 6,450,163 B1 * | 9/2002 | Blacker et al. ............ 128/200.18 |
| 6,595,203 B1 * | 7/2003 | Bird ........................ 128/200.21 |
| 6,644,304 B2 | | 11/2003 | Grychowski |
| 6,772,754 B1 | | 8/2004 | Mendenhall |
| 7,080,643 B2 | | 7/2006 | Grychowski |
| 7,270,123 B2 * | 9/2007 | Grychowski et al. ..... 128/200.14 |
| RE40,591 E * | 12/2008 | Denyer .................... 128/200.18 |
| 8,113,194 B2 * | 2/2012 | Boehm et al. ............. 128/200.18 |
| 2002/0157663 A1 * | 10/2002 | Blacker et al. ............ 128/200.21 |
| 2003/0136399 A1 | | 7/2003 | Foley |
| 2004/0173209 A1 * | 9/2004 | Grychowski et al. ..... 128/200.21 |

* cited by examiner

*Primary Examiner* — Lynne Anderson
*Assistant Examiner* — Bradley Philips

(57) ABSTRACT

The present invention is directed generally to a nebulizer for the formation of micro-droplets from liquid medicaments for respiratory patient treatment, and more specifically, to a baffled nebulizer wherein a static baffle used to form an atomized medicament is proximal to a shied which responds to patient respiration force to oscillate from an aerosol flow occluding position to an aerosol flow open position. During inhalation, the shield moves into a first registration format to allow passage of the atomized medicament (nebula) to the patient. During exhalation/non-use, a biasing pressure maintains said shield in a second registration format such that the nebula is retarded from passing to the patient and is coalesced into macro-droplets which return to a supply reservoir for re-atomization. The present nebulizer design is particularly adaptable for controlling atomization in response to patient respiratory forces exceeding a defined threshold; allowing for opportunity to control inhalation airflow and enhanced therapy regimes.

19 Claims, 16 Drawing Sheets

INHALATION ACTUATED NEBULIZER WITH IMPINGEMENT SHIELD

CROSS-REFERENCE TO RELATED APPLICATIONS

This application claims the benefit under 35 U.S.C. 119(e) of U.S. provisional application Ser. No. 61/281,402 filed Nov. 16, 2009, which is incorporated by reference herein in its entirety

STATEMENT REGARDING FEDERALLY SPONSORED RESEARCH

Not Applicable

BACKGROUND OF THE INVENTION

Nebulizers for producing micro-droplets (i.e. aerosol) from liquid medicaments and presenting those aerosols for patient respiratory therapy are a well-known and practiced technology. A typical nebulizer design includes the basic elements of a gas inlet port, a respirable gas outlet, a liquid reservoir and a means for forming micro-droplets of the liquid within the reservoir. Early designs, such as represented by U.S. Pat. No. 3,097,645 and U.S. Pat. No. 3,762,409, both to Lester and incorporated by reference in their entireties herein, depict the basic elements of a typical constant-flow type nebulizer. Constant-flow type nebulizers create micro-droplets of liquid medicament based on an uninterrupted supply of pressurized gas coming through the gas inlet port and entraining liquid from the reservoir continually, forming a fraction of the liquid into an aerosol until such time the pressurized gas is stopped or the reservoir of liquid becomes empty. While representative simple nebulizers such as taught by Lester are capable of producing an aerosol, the efficiency of simply jetting an entrained liquid stream into a free space was not found to be adequate for creating micro-droplets of a consistent size and rate. U.S. Pat. No. 4,588,129 to Shanks, incorporated herein by reference in its entirety, addresses this consistent size and rate issue of the earlier Lester designs by further incorporating a fixed baffle having a convex target surface. In the Shanks nebulizer, a liquid entrained jet stream strikes upon the convex target surface of the baffle and the impact thereof allows for the momentum imbued within the liquid stream to mechanically act upon the stream and cause the creation of smaller, more readily inhaled micro-droplets at a higher rate.

The Lester and Shanks nebulizers greatly advanced the art of aerosol formation, however, due to their continuous aerosol formation mode of operation, much of the liquid medicament formed into an aerosol was lost from the device during patient exhalation and idle operation of the device. Loss of aerosolized medicament to the environment is deleterious as there is a decrease in therapeutic value to the patient resulting from reduced dosing, as well as, contamination of the immediate atmospheric environment and inadvertent dosing of individuals not requiring treatment. Dosing variability with continuous aerosol formation nebulizers is also very high and largely affected by the physiological respiratory of the patient, thus two different patients with two different inhalation and exhalation time ratios using the same continuous aerosol formation nebulizer will receive significantly different doses. Improvements were then made to alter nebulizer performance such that the creation of micro-droplets through aerosolization occurred only when the patient being treated was inhaling through the nebulizer. Published U.S. Patent Application 2003/0136399 to Foley, et al., teaches a means for a nebulizer, which creates a constant micro-droplet aerosol within a closed chamber, which is released through operation of a valve. Published U.S. Patent Application 2002/0157663 to Blacker, et al., seeks to control aerosol production through patient inhalation completing the path from the liquid reservoir to the entrainment orifice and thereby allow liquid to entrain into the pressurized gas. U.S. Pat. No. 7,080,643 to Grychowski, et al., utilizes a gas diverter, which moves into and out of position wherein pressurized gas is directed across liquid transfer conduits and the vacuum created thereby causes liquid to be drawn through the transfer conduits and entrained into the gas flow. The aforementioned U.S. patent numbers are incorporated herein in their respective entireties.

Although many of the problems of continuous nebulizers has been mitigated by various clinical practices, the nature of medications needed to be aerosolized for inhalation by patient has begun to change such that there is a greater need for control of dosing and environmental exposure. Previously, aerosolized medications were primarily aqueous solutions containing low mass concentrations of salts or other easily soluble compounds with wide allowable dosing profiles and low toxicities. A number of new medication have begun to be introduced, including some consisting of proteins and other biological material, that have much tighter allowable dosing profiles, greater toxicity risks, and greater concern of secondary exposure of un-intended individuals present during treatment due to exposure to exhaled aerosolized medication or aerosolized medication produced at some other time than inhalation. Some of these newer medications tend to have a much higher mass concentrations resulting in thicker solutions and higher viscosities. The result is that much more residual material may be caused to accumulate in or around the nozzle, which can impede or prevent the proper performance of the nebulizer over the course of treatment. Accumulation of material around the nebulizer nozzle, thus impeding performance, is a particular problem with nebulizers that are breath-actuated through means that include intermittently turning on and off gas or liquid flow in synchronization with patient respiration, due to the enhanced drying effect realized by these strategies. Dosing of these medications is many times a much more sensitive issue than older medications, thus a nebulizer that delivers medication only upon inhalation has a distinct advantage over those that run continuously, because inhalation and exhalation time ratios can vary tremendously from patient to patient, thus a breath actuated nebulizer can deliver a more consistent dose regardless of respiration pattern. Furthermore, breath-actuated nebulizers may help mitigate secondary exposure issues by insuring that aerosol is produced only during inhalation, although it is well known that patients will exhale some of the aerosolized medication that has been inhaled and a breath-actuated nebulizer by itself does not completely solve the problem of secondary exposure. Unfortunately, if nebulizer performance is degraded due to accumulation of medication in or around the nozzle, the benefits of breath-actuation can be largely offset by the degraded performance of the nebulizer. Therefore a need exists for a breath-actuated nebulizer that is less sensitive to material accumulation of large molecule medications, that is designed primarily for delivery during patient inhalation, and which has a design that lends itself to mitigation and control of secondary exposure.

Many existing breath-actuated nebulizer involve electrical or sophisticated mechanical components necessary to detect patient inhalation. These devices suffer from high purchase price associated with added sophistication and the inconvenience of a re-usable component that needs to be stored, retained, set up, and cleaned with each use. Therefore a need also exists for a breath-actuated device that is simple in design and capable of being entirely made out of inexpensive parts and therefore potentially for single use and disposable.

The present invention satisfies all of these referenced needs.

BRIEF SUMMARY OF THE INVENTION

The present invention is directed generally to a nebulizer for the formation of micro-droplets (i.e. aerosol) from liquid medicaments for respiratory patient treatment, and more specifically, to a baffled nebulizer wherein a static baffle used to form an atomized medicament is proximal to a shield which responds to patient respiration force to oscillate from an occluding position to an open flow position. An entrainment orifice within the nebulizer utilizes pressurized gas to draw in liquid medicament from a reservoir and to entrain that liquid medicament into a continuous high velocity stream. The high velocity liquid entrained jet is oriented such that an optimization point is achieved continuously at a defined distance in front of the entrainment orifice. A target surface is positioned at the optimization point of the high velocity jet such that the medicament within the stream is atomized into micro-droplets. When the shield is in a first position, the atomized medicament impinges upon the shield, losing jet momentum, which causes the micro-droplets to coalesce into macro-droplets that are non-respirable and return to the liquid reservoir for re-entrainment. Since the nozzle is continuously entraining and processing medication during this time, although not forming aerosol due the position of the shield, medication is continuously cycled through the nozzle region and there is little drying and little or no residual build up of thick and viscous medications. Thus the invention is less sensitive to mass accumulation and is more able to consistently deliver large molecule, high concentration, and/or more viscous medications. When the shield is in a second position, the micro-droplets are un-occluded and are released into aerosol outlet which then may be inhaled by the patient. The impingement shield moves between the first and second positions based upon the respiration of the patient, thus moving the impingement shield into the second position only when patient inhalation occurs, thereby preventing excessive waste of liquid medicament, improving patient therapy, mitigating the accumulation of medication around the aerosol producing region, mitigating secondary disposable, and doing so in a simple enough manner to lend itself well to a inexpensive and disposable device.

A nebulizer assembly made in accordance with instant disclosure is capable of an expulsion rate of equal to or greater than 1.0 ml per minute at a gas flow rate of greater than 8 liters per minute and pressures of between 15 and 50 psig. The high performance of the impingement shield nebulizer at low pressures is significant in that conventional nebulizer compressors as used in home administrated therapy exhibit a pressure output of between 15 to 20 psig, a pressure range in which other nebulizer technologies exhibit diminished expulsion rates, thus requiring additional time of dosing and less than optimum aerosol particle size.

In a further embodiment of the present invention, the nebulizer assembly is particularly adapted to control atomization in response to patient respiratory forces exceeding a defined threshold. The impingement shield is operably associated with an intake valve such that when a negative threshold pressure is attained within the nebulizer, such as provided by an inhalation force provided by a respiring patient, said intake valve is moved from a closed to an open state establishing inhalation flow through the nebulizer. By rendering the air flow through the nebulizer as contingent upon exceeding a minimum negative pressure it is now possible to constrain atomization of a medicament to the combined operational status of the patient inhaling (to actuate the impingement shield into a second "open" or non-occluding state) and of the patient attaining a defined level of force during inhalation (allowing for opportunity to control inhalation airflow to coincide with deeper pulmonary penetration of medicinal nebula), thus offering enhanced therapy regimes. This combined operational status is particularly noteworthy in that prior art devices will not produce aerosol until there floating baffle is drawn all the way down, which is achieved only upon reaching a minimum inhalation vacuum pressure, the result of which is that it is possible with prior art devices for a patient to breath at a low inhalation flow rate insufficient to draw the floating baffle all the way down so that aerosol is produced. The unique and novel design of the current invention disallows any flow of air through the nebulizer until such time that shield has been drawn down, thus providing greater assurance that aerosol is delivered with each inhalation and being suitable for a broader range of patients. Because the current invention is suitable for a broad range of flow rates, it can be fabricated into a form with a very low nebulization flow rate (e.g. 1.0 l/min) that will maximize its sensitivity to the inhalation effort of the patient.

In a further embodiment of the present invention, the nebulizer having a respiration responsive impingement shield as presented herein may further include an electronic sensor which is responsive to the position and duration of the impingement shield being in said first and second positions. By using a simple and conventional logic circuit, it is possible to indicate to the patient if insufficient inhalation or exhalation periods of occurred. The same logic circuit can be used to indicate optimum therapy duration to the patient, possible error conditions, or provide estimated dosages by flagging of visual and/or auditory cues. The same logic circuit can be used to transmit the same resulting information through electrically conducting or wireless means to a remote location for use as a clinical evaluation tool or to provide greater management of a patient's condition.

DESCRIPTION OF THE SEVERAL VIEWS OF THE DRAWING(S)

The invention will be more easily understood by a detailed explanation of the invention including drawings. Accordingly, drawings, which are particularly suited for explaining the inventions, are attached herewith; however, it should be understood that such drawings are for descriptive purposes only and as thus are not necessarily to scale beyond the measurements provided. The drawings are briefly described as follows.

LIST OF REFERENCE NUMERALS

Figure 1:
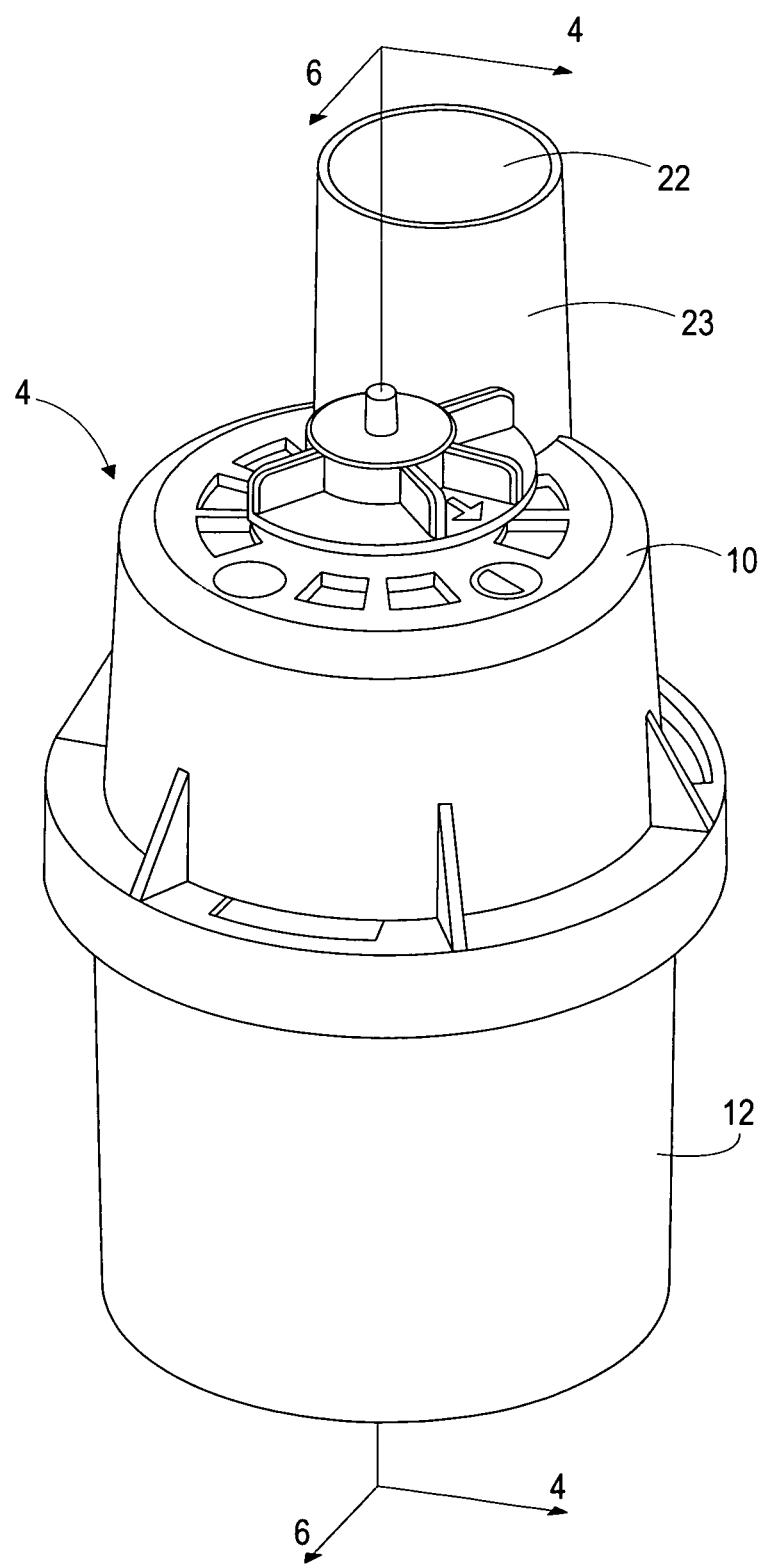
FIG. 1 is an exterior perspective view of an inhalation-controlled nebulizer in accordance with the present invention, wherein cross-sectional planes 3-3 and 4-4 are defined.
Figure 2:
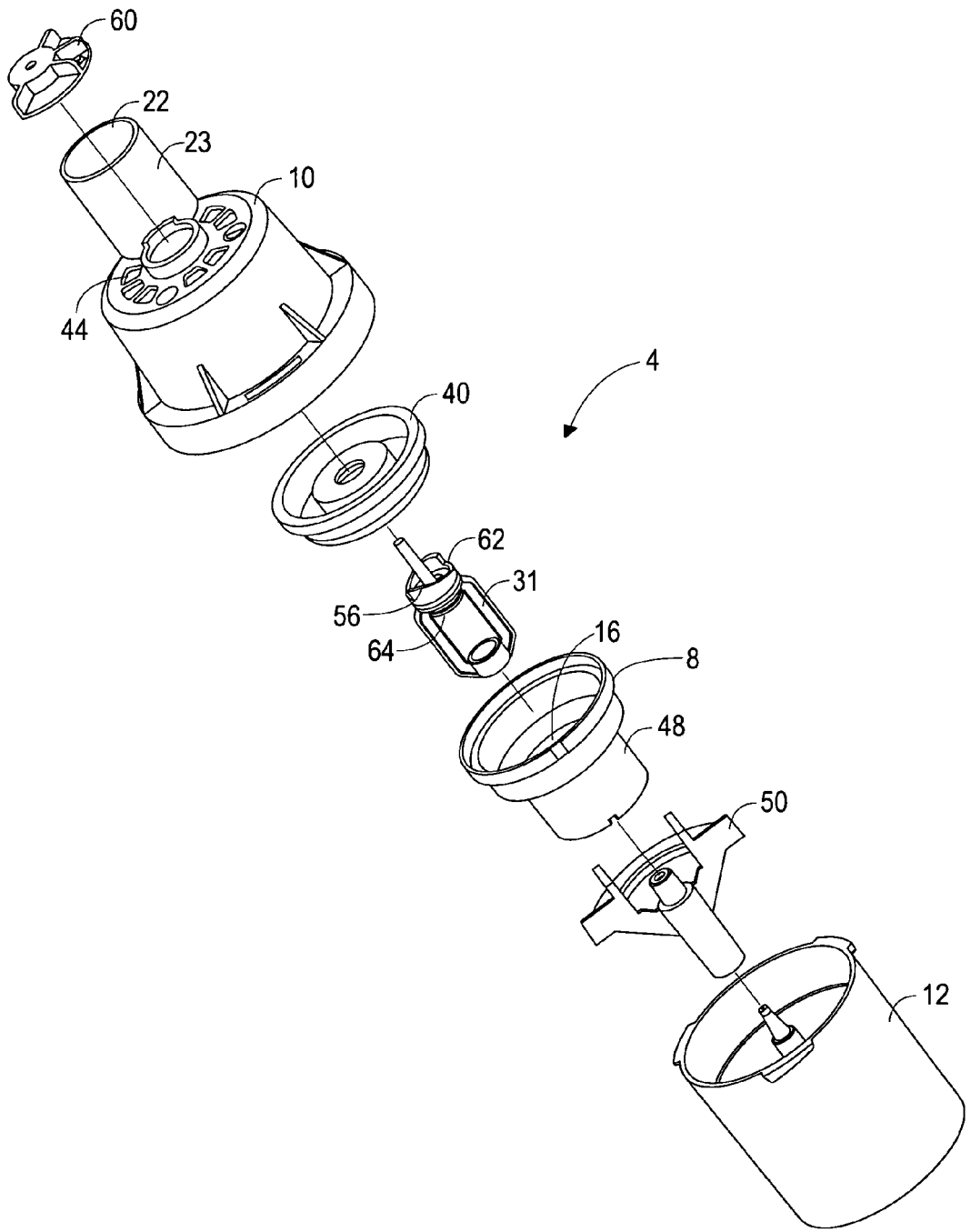
FIG. 2 is an exploded perspective view of an inhalation controlled nebulizer as presented in FIG. 1, wherein the impingement shield is presented.
Figure 3:
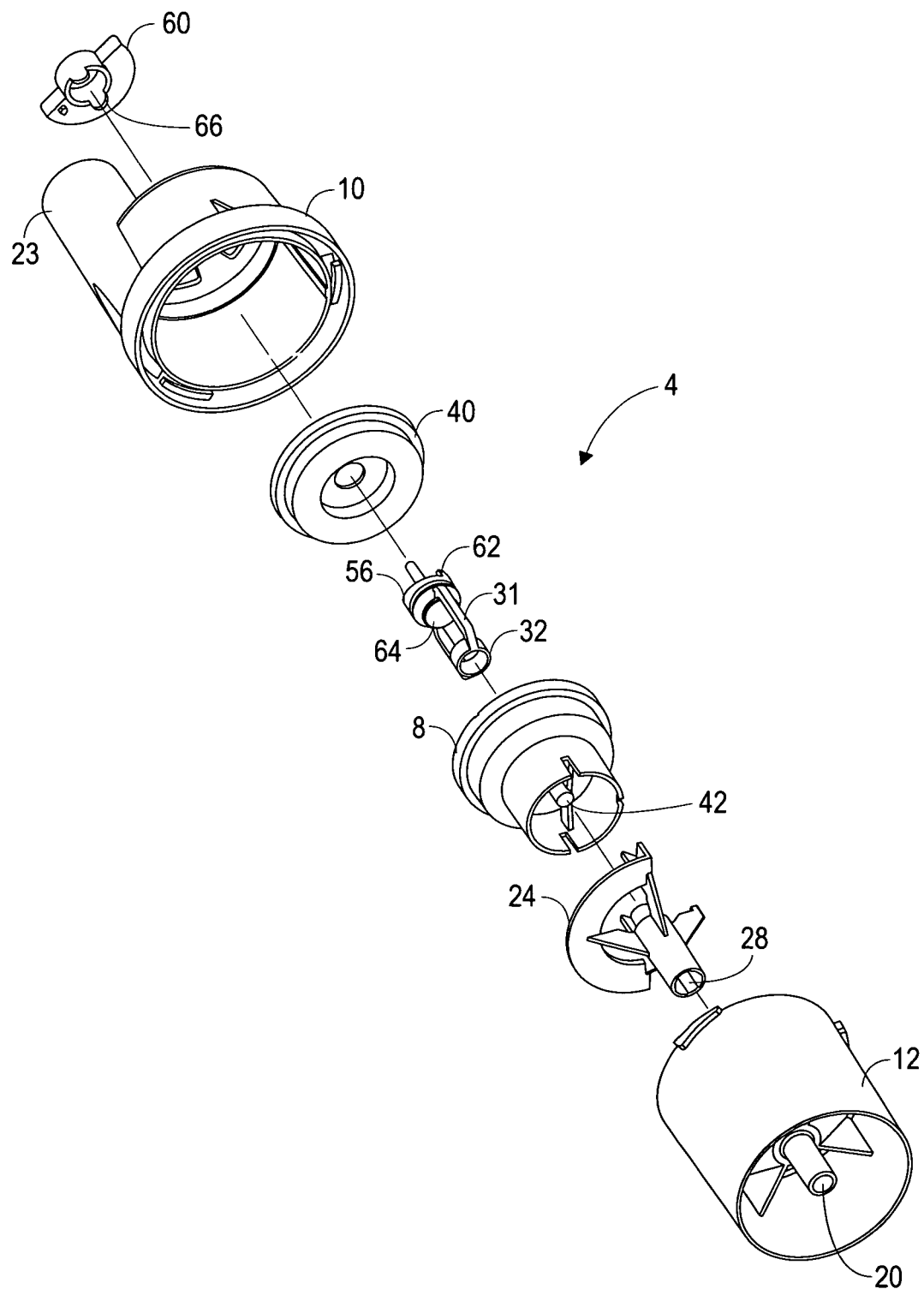
FIG. 3 is an exploded perspective view of an inhalation controlled nebulizer as presented in FIG. 1, wherein the impingement shield is presented.

| | |
|---|---|
| 4 | Nebulizer Unit |
| 6 | Patient Tee Assembly |
| 8 | Insert |
| 10 | Upper Chamber |
| 12 | Lower Chamber |
| 14 | Liquid Reservoir |
| 16 | Aerosol Chamber |
| 18 | Internal Gas Conduit |
| 20 | Gas Inlet Port |
| 22 | Aerosol Outlet Port |
| 23 | Nebulizer Outlet Body |
| 24 | Secondary Shroud |
| 26 | Entrainment Orifice |
| 28 | Liquid Transfer Channels |
| 30 | Jet Orifice |
| 31 | Shield Assembly |
| 32 | Impingement Shield |
| 33 | Shield Yoke |
| 34 | Shield Flag |
| 36 | Yoke Mounting Flange |
| 40 | Biasing Support |
| 42 | Target Surface |
| 44 | Air Inlet Portal |
| 46 | Retention Ring |
| 48 | Liquid Backflow Guard |
| 50 | Nozzle Yoke |
| 52 | Ambient Chamber |
| 54 | Cylindrical Guide |
| 56 | Shield Cam |
| 58 | Shield Flow Ports |
| 60 | Adjustment Knob |
| 62 | Shield Minimum Flow Channel |
| 64 | Shield Flow Diverter |
| 66 | Adjustment Knob Actuating Teeth |
| 68 | Intermittent Ambient Gas Passage |
| 70 | Post Nebulization Filter |
| 72 | Mouthpiece |
| 74 | Nebulizer Tee |
| 76 | Check Valve Body |
| 78 | Check Valve Flapper |
| 80 | Filter Membrane |
| 82 | Mouthpiece Conduit |
| 84 | Mouthpiece Port |
| 86 | Nebulizer Port |
| 88 | Anti-Drool Chimney |
| 90 | Check Valve Port |
| 92 | Check Valve Flow Conduits |
| 94 | Flapper Retention Boss |
| 96 | Flapper Retention Orifice |

DETAILED DESCRIPTION OF THE INVENTION

While the present invention is susceptible of embodiment in various forms, there is shown in the drawings and will hereinafter be described a presently preferred embodiment of the invention, with the understanding that the present disclosure is to be considered as an exemplification of the invention, and is not intended to limit the invention to the specific embodiment illustrated.

Referring more specifically to the figures, for illustrative purposes the present invention is embodied in the apparatus generally shown in FIG. 1 through FIG. 16.

In FIG. 1 through 8, therein is depicted nebulizer unit 4. Nebulizer unit 4 is comprised of an upper chamber 10 and a lower chamber 12. Upper chamber 10 has therein an insert 8 for allowing ambient air to be drawn through aerosol chamber 16, chamber 10 and an aerosol outlet port 22 having a liquid backflow guard 48, which is in fluid communication with a patient through a suitable mouth piece, mask, endotracheal tube, or patient tee assembly 6 as shown if FIG. 13 through 16. Lower chamber 12 has therein a liquid reservoir 14 and a gas inlet port 20. Gas inlet port 20 extends from an area exterior to lower chamber 12 whereby it is attached to a pressurized gas supply (not shown) and passes through liquid reservoir 14, into secondary shroud 24. In the embodiment shown, upper chamber 10 and lower chamber 12 are releasably affixed to one another so that liquid medicament can be introduced into liquid reservoir 14. It is within the purview of the present invention that a liquid addition portal can be provided for introduction of liquid medicament, and in such case, upper chamber and lower chamber may be permanently affixed at the time of manufacture.

Figure 4:
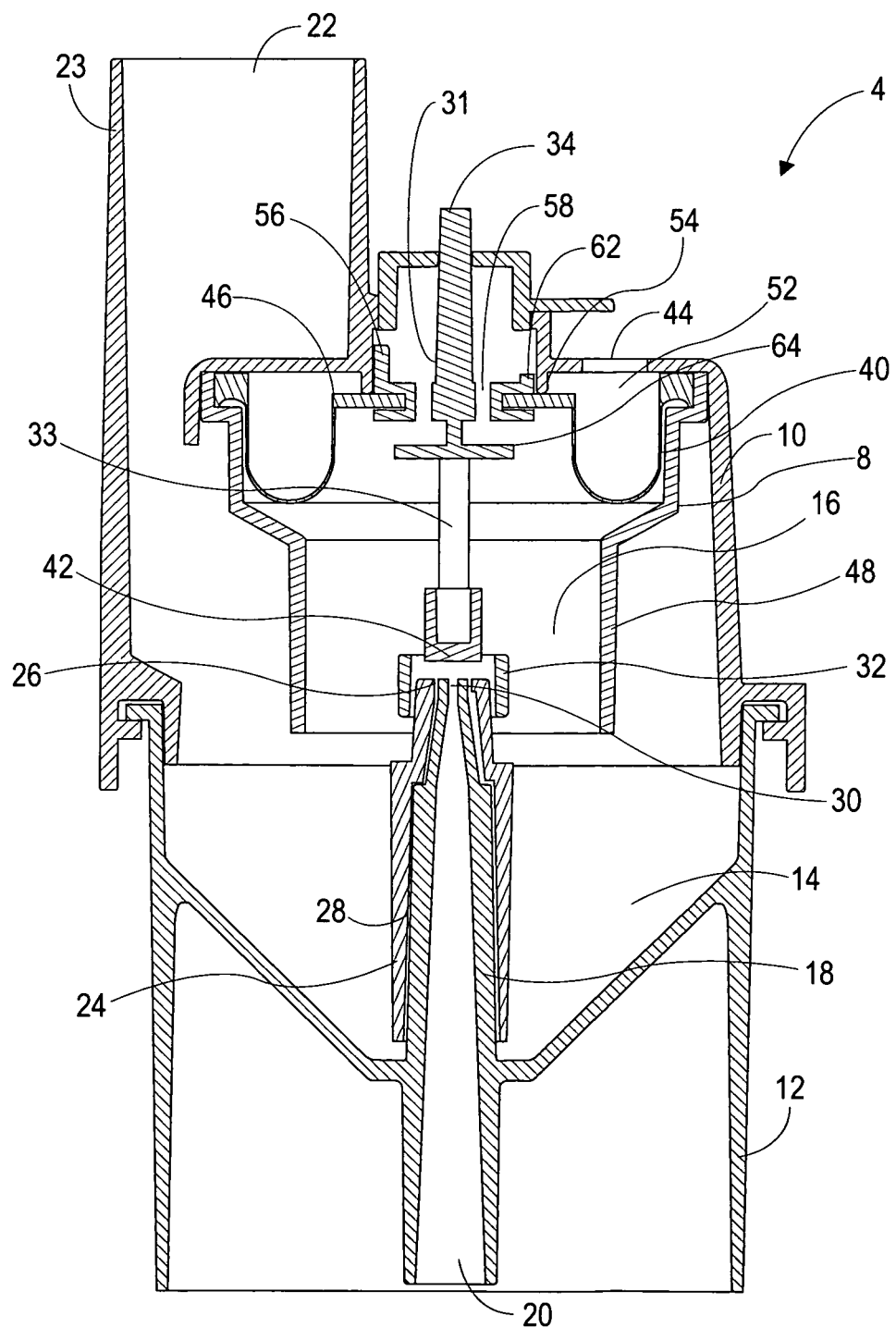
FIG. 4 is a cross sectional side view of an inhalation controlled nebulizer with impingement shield in a non-aerosol producing position taken along line 3-3.
Figure 5:
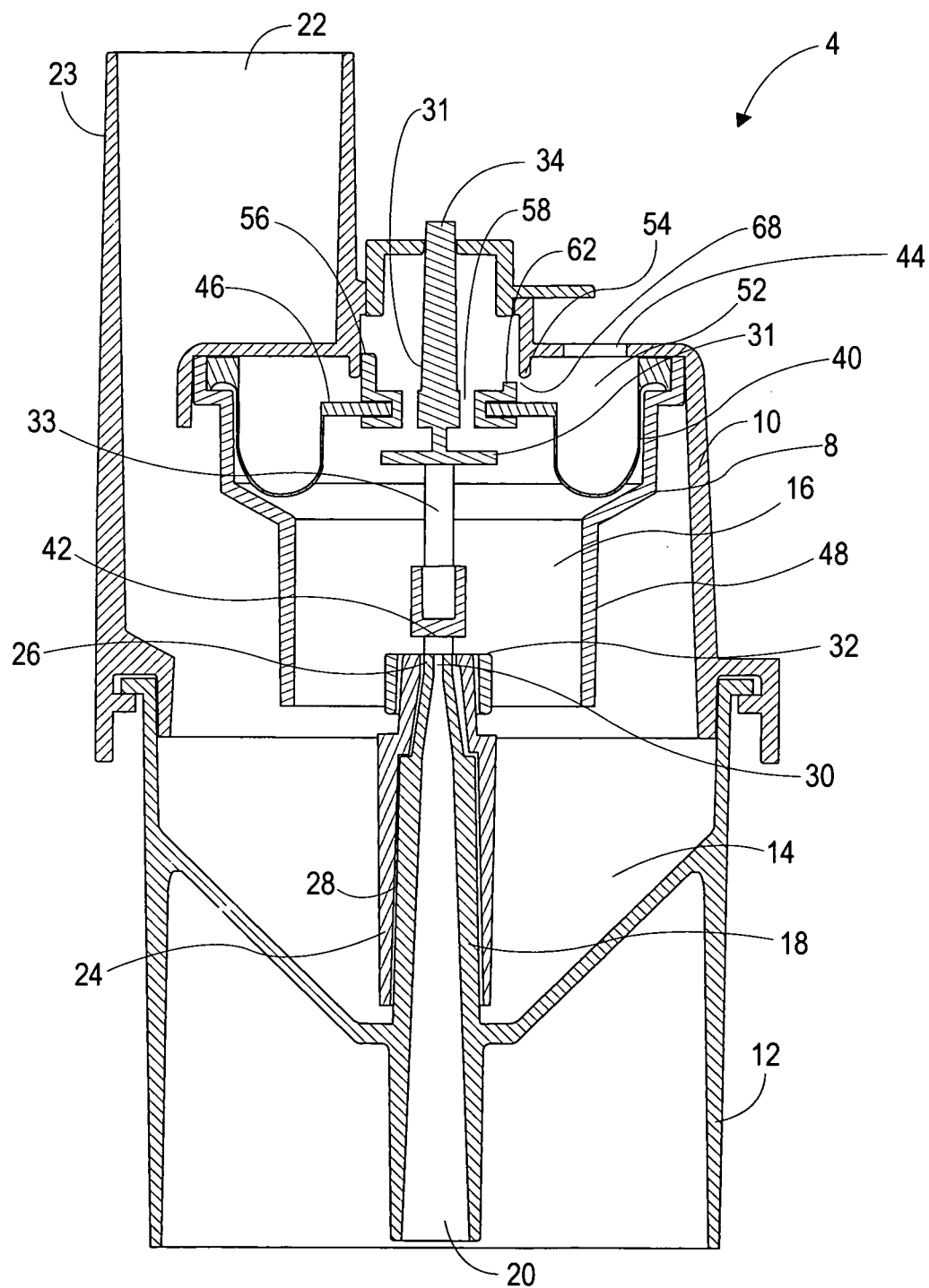
FIG. 5 is a cross sectional side view of an inhalation controlled nebulizer with impingement shield in an aerosol producing position taken along line 3-3.
Figure 6:
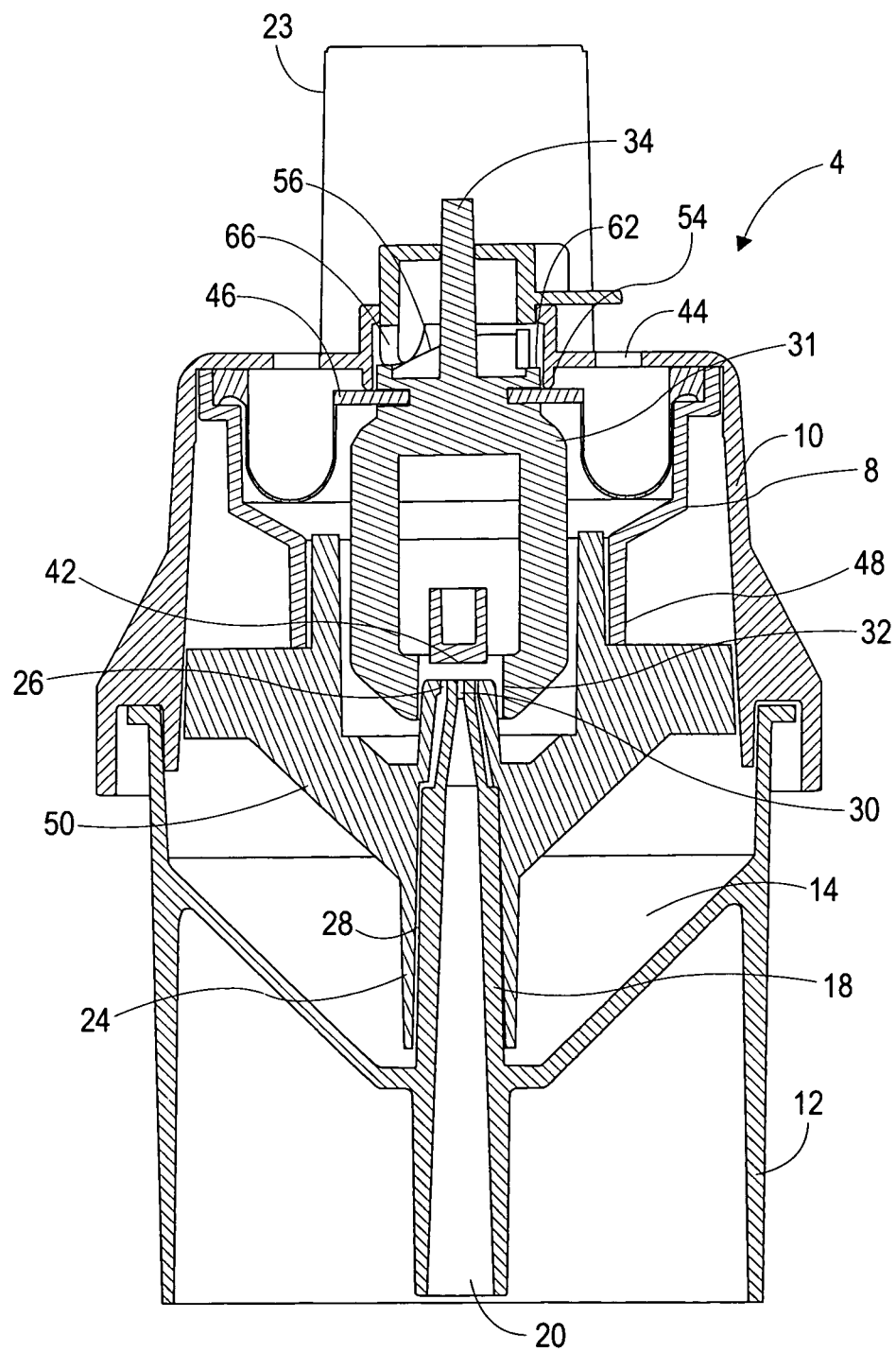
FIG. 6 is a cross sectional side view of an inhalation controlled nebulizer with impingement shield in a non-aerosol producing position taken along line 4-4.
Figure 7:
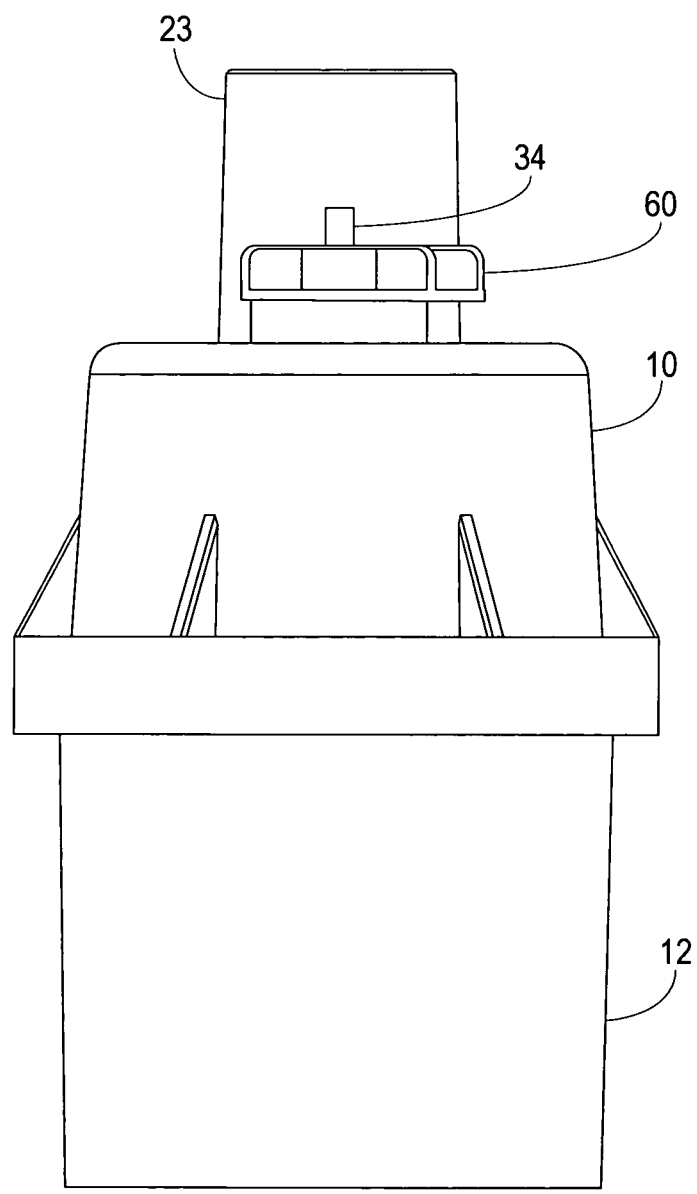
FIG. 7 is a left side view of an inhalation controlled nebulizer with impingement shield.
Figure 8:
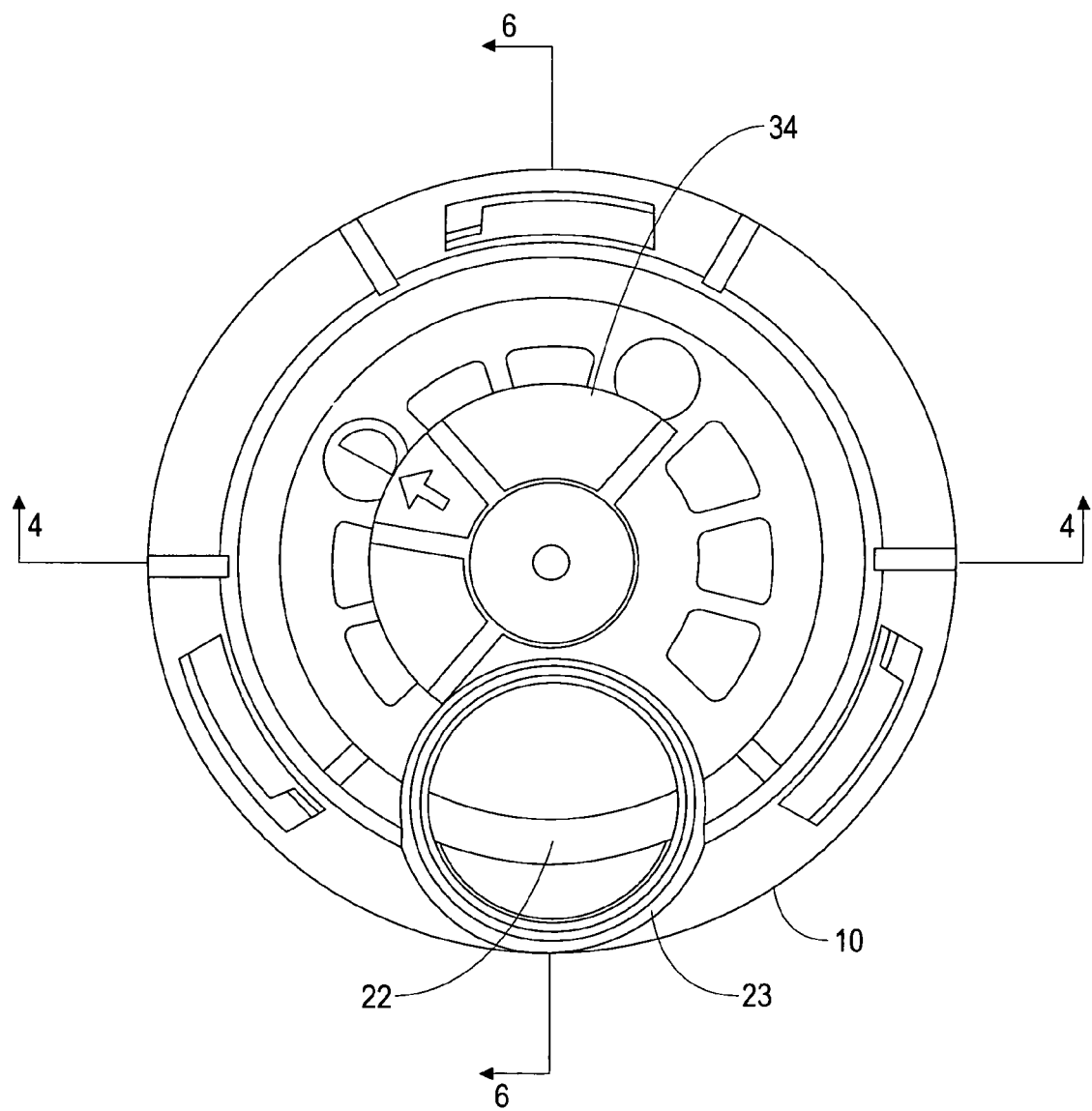
FIG. 8 is a top end view of an inhalation controlled nebulizer with impingement shield.
Figure 9:
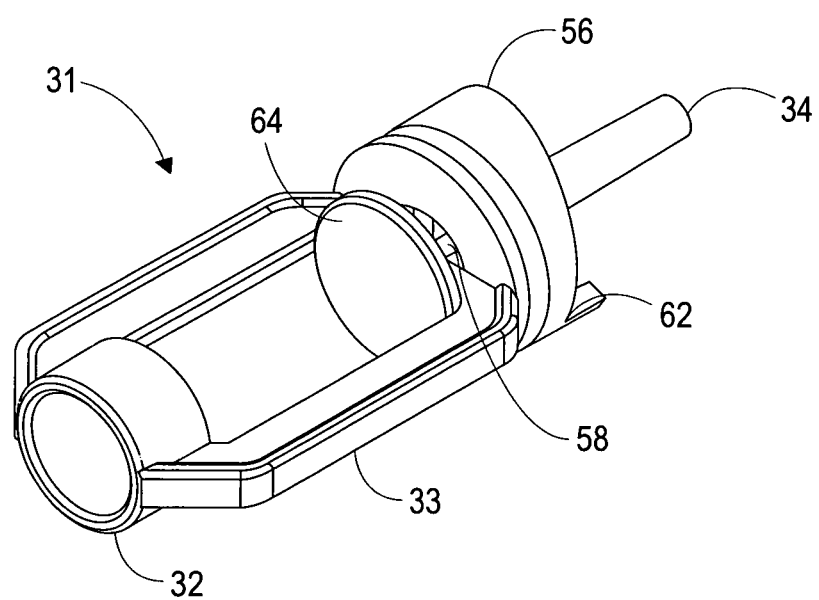
FIG. 9 is a perspective view of shield assembly with impingement shield.

Turning to FIGS. 4, 5, and 6, therein is depicted secondary shroud 24 comprising a liquid transfer conduit 28, jet orifice 30, internal gas conduit 18, and an orientation and construction support member nozzle yoke 50. Gas provided to gas inlet port 20 is caused to pass through internal gas conduit 18 and onto jet orifice 30, where with sufficient gas pressure (greater than 8 psig) provided to gas inlet port 20, the gas jet emanating from jet orifice 30 will be a significant percentage of or be equal to the speed of sound. Liquid transfer conduit 28 forms an interstitial space between the external geometry of internal gas conduit 18 and the internal geometry of secondary shroud 24 and necessarily provides a free flowing path for liquid from the bottom of liquid reservoir 14 and entrainment orifice 26. Secondary shroud 24 utilizes pressurized gas from gas inlet port 20 ejected through jet orifice 30 onto target surface 42, wherein the proximity of surface 42 is sufficient to redirect the flow of the impinging gas radially thereby causing a vacuum across a proximal opening of entrainment orifice 26, thus drawing liquid medicament from liquid reservoir 14 through liquid transfer conduit 28 and to entrain that liquid medicament into a continuous high velocity atomized radial fan. Although other nozzle configurations are also possible with the present invention, as exemplified in FIGS. 10, 11, and 12, the fan shaped spray produced by the described nozzle has been found to be desirable. By way of the fluidic jet stream impacting upon target surface 42 and through the combined actions of jet dispersion, high jet momentum, and shear forces acting on introduced fluid, micro-droplets of liquid medicament are formed so long as there is liquid medicament to be entrained and a supply of gas through gas inlet port 20. Target surface 42 may have a simple geometric or radiused cross sectional profile as well as compound combinations of differing geometric and/or radiused cross sectional profiles. In a preferred embodiment, target surface is of a flat, convex or hemispherical cross sectional profile.

Positioned proximal to the target surface 42 is impingement shield 32. Impingement shield 32 is capable of at least partially occluding the fluidic communication pathway between a nebulization area defined as the region between entrainment orifice 26 and fixed target surface 42, and aerosol chamber 16 that is internal to insert 8. When impingement shield 32 is in first position, the fluidic communication pathway between the nebulization area and aerosol chamber 16 is at least partially occluded. When the fluidic communication pathway is at least partially occluded by impingement shield 32, micro-droplets produced by the interaction of entrainment orifice 26 with target surface 42 are slowed and the majority is caused to impact upon the impingement shield 32. As micro-droplets of medicament are slowed and may impact upon the impingement shield 32, the micro-droplets coalesce into macro-droplets, which in turn are un-respirable and return under gravity to liquid reservoir 14. Impingement shield 32 can also be translated to a second position, wherein the fluidic communication pathway between the nebulization area and aerosol chamber 16 is not occluded, thus allowing micro-droplets of medicament to be released into aerosol chamber 16. As a patient breathes, the impingement shield 32 oscillates between the first and second position. Although the geometry needed for impingement shield 32 to be effective at obstructing the flow of aerosol from the nebulization area to aerosol chamber 16 when obstruction is desired varies, it is preferred that impingement shield 32 be of sufficient height and placement in the obstructing position that the direction of travel of gas originating from jet orifice 30, redirected by target surface 42, and emanating from the nebulizer area be caused to change as a result of impingement shield 32 position prior to entering aerosol chamber 16. It is furthermore preferred that the geometry around the nebulization area when impingement shield 32 is in an obstructing position redirect the gas stream preferentially upwards against the flow of gravity. In such manner, coalesced liquid accumulates to a greater degree within impingement shield 32 and around nebulization area, providing greater efficiency at the capture of aerosol particles leaving nebulization area and thereby causing a greater return of liquid medication to the reservoir.

Figure 10:
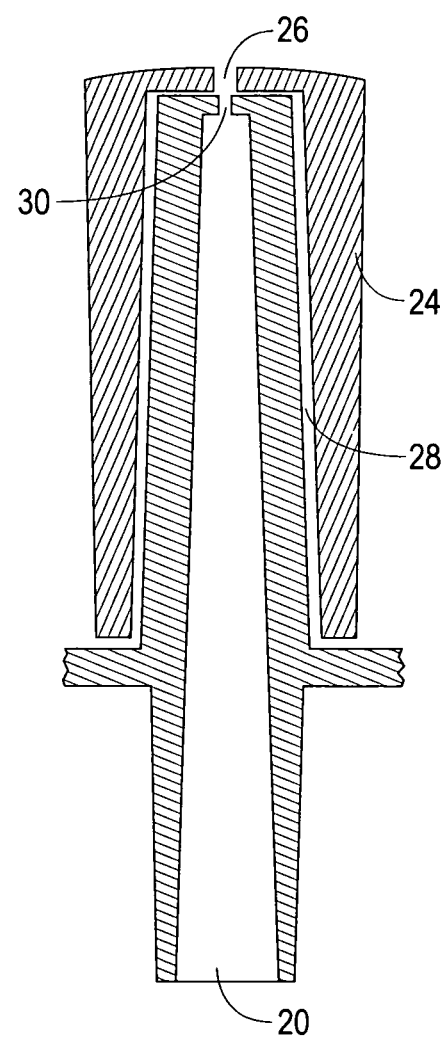
FIG. 10 is a sectional view of an alternate nozzle design applicable for use in an inhalation controlled nebulizer with impingement shield.

In an alternative design, secondary shroud 24 may comprise entrainment orifice 26, liquid transfer conduit 28, and jet orifice 30 (FIG. 10). In accordance with the ejection nozzles taught by Lester in the aforementioned and incorporated patents of reference, as pressurized gas issues from jet orifice 30 into entrainment orifice 26, liquid from reservoir 14 is drawn up liquid transfer conduit 28. As liquid is drawn through liquid transfer conduit 28, it passes through a flow control point (typically about 0.010 inch in height) and then into direct contact with, and becomes entrained within, the gas issuing from jet orifice 30 and is forcibly ejected from entrainment orifice 26 as a focused continuous stream of liquid entrained gas. The high velocity liquid entrained jet is oriented such that an optimized focal point is continuously achieved at a defined distance from the entrainment orifice 26. As the liquid jet stream comes to the optimization point of the jet, the jet strikes a fixed target surface 42. The liquid jet stream impacting upon target surface 42, and through the combined actions of minimal jet dispersion and high jet momentum forms micro-droplets of liquid medicament so long as there is liquid medicament to be entrained and a supply of gas through gas inlet port 20. It is within the purview of the present invention that one or more liquid entrained gas jets may be formed by secondary shroud 24. The nozzle configuration of FIG. 10 is suitable with an array of different target surface 42 geometries including the hemispherical design shown in FIG. 11, and the flat disc design shown in FIG. 12.

Within a central region of upper chamber 10, there extends downwardly insert 8. Insert 8 may be either an element integral to upper chamber 10 or separate element affixed to a central void within upper chamber 10. In a preferred embodiment, insert 8 is generally round in cross section taken at a point parallel to a point of junction with lower chamber 12. The insert 8 extends into a central void of upper chamber 10 and has a distal point that is proximal to secondary shroud 24. At the distal point of insert 8 therein is an optional retention ring 46 that acts upon shield assembly 31 to maintain durable attachment to a biasing support 40.

Figure 11:
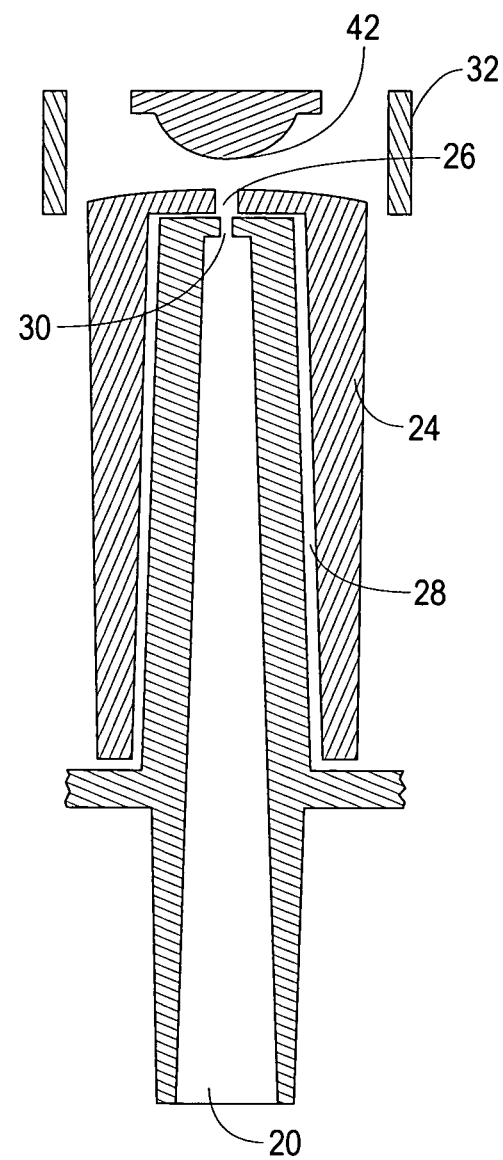
FIG. 11 is a sectional view of an alternate nozzle design, hemispherical target surface, and impingement shield in a non-aerosol producing position applicable for use in an inhalation controlled nebulizer with impingement shield.
Figure 12:
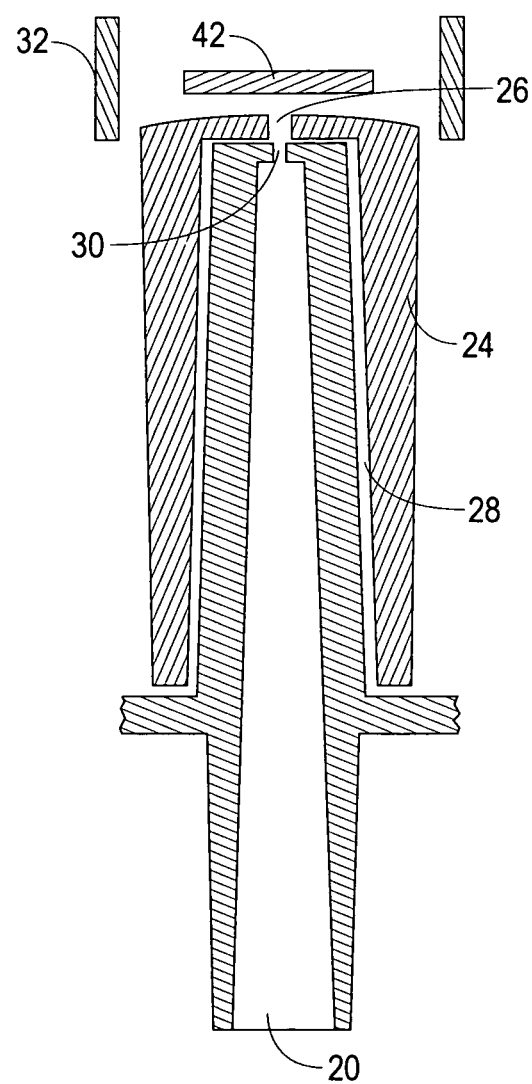
FIG. 12 is a sectional view of an alternate nozzle design, flat target surface, and impingement shield in a non-aerosol producing position applicable for use in an inhalation controlled nebulizer with impingement shield.
Figure 13:
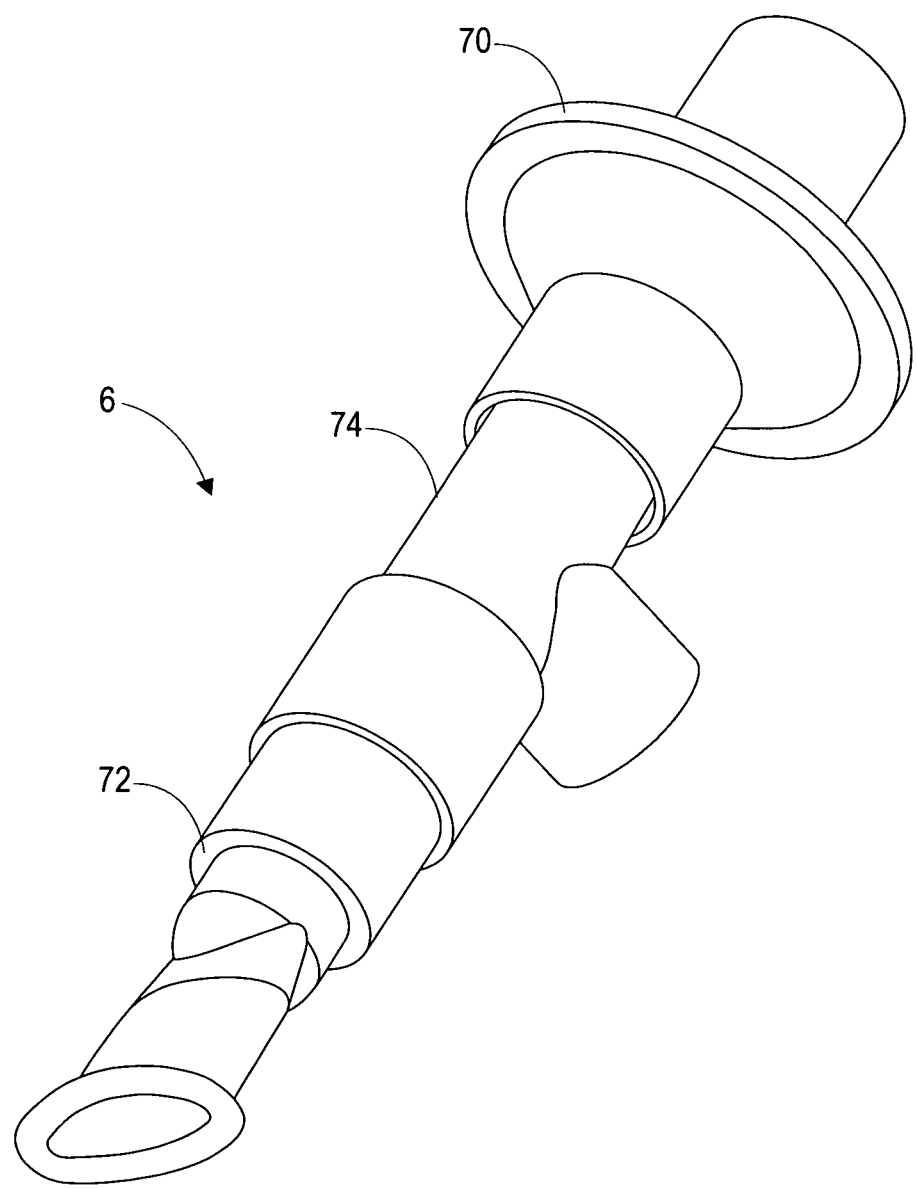
FIG. 13 is a perspective view of a patient tee assembly equipped with nebulizer tee, mouthpiece and exhalation filter.
Figure 14:
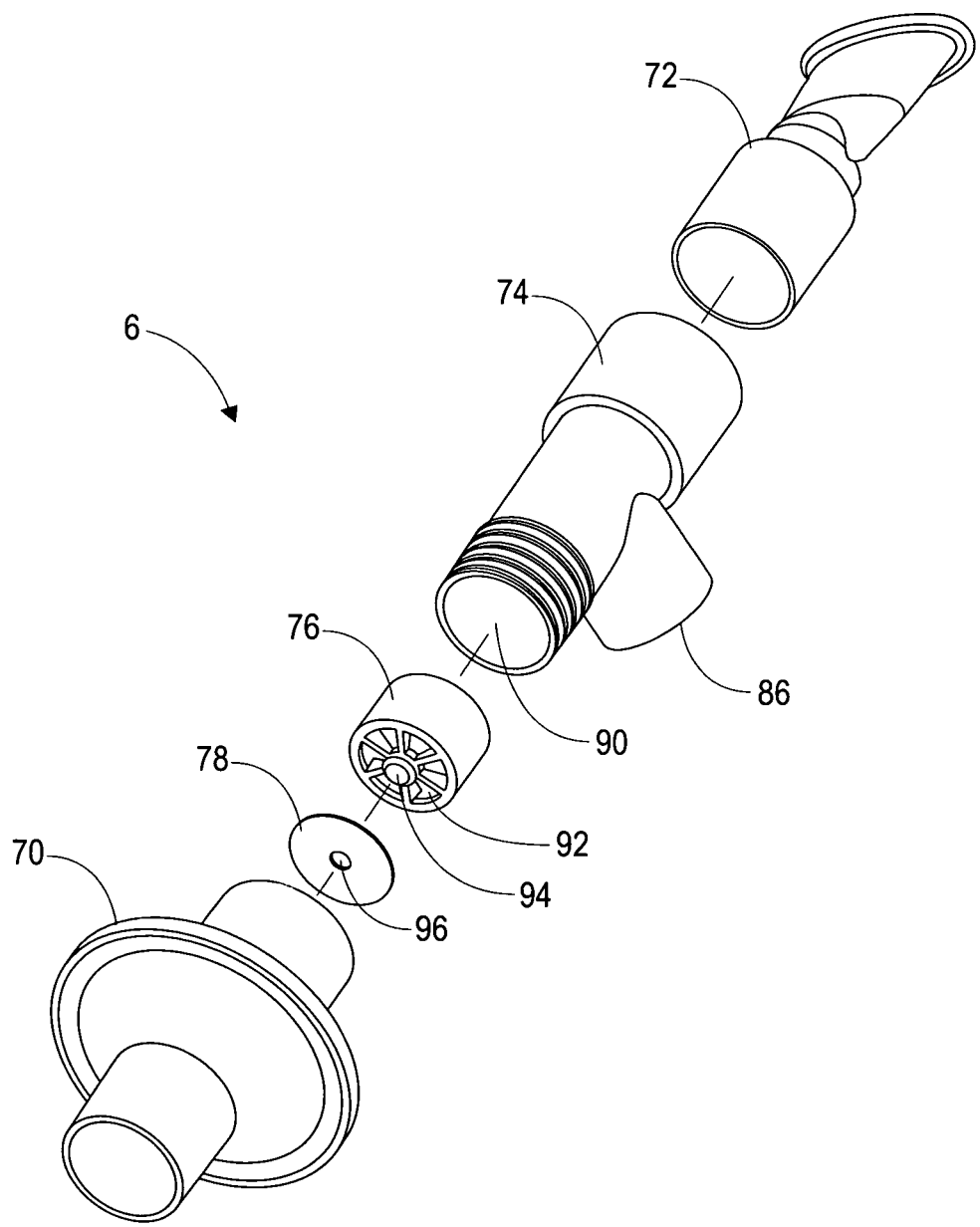
FIG. 14 is an exploded perspective view of a patient tee assembly equipped with nebulizer tee, mouthpiece and exhalation filter.
Figure 15:
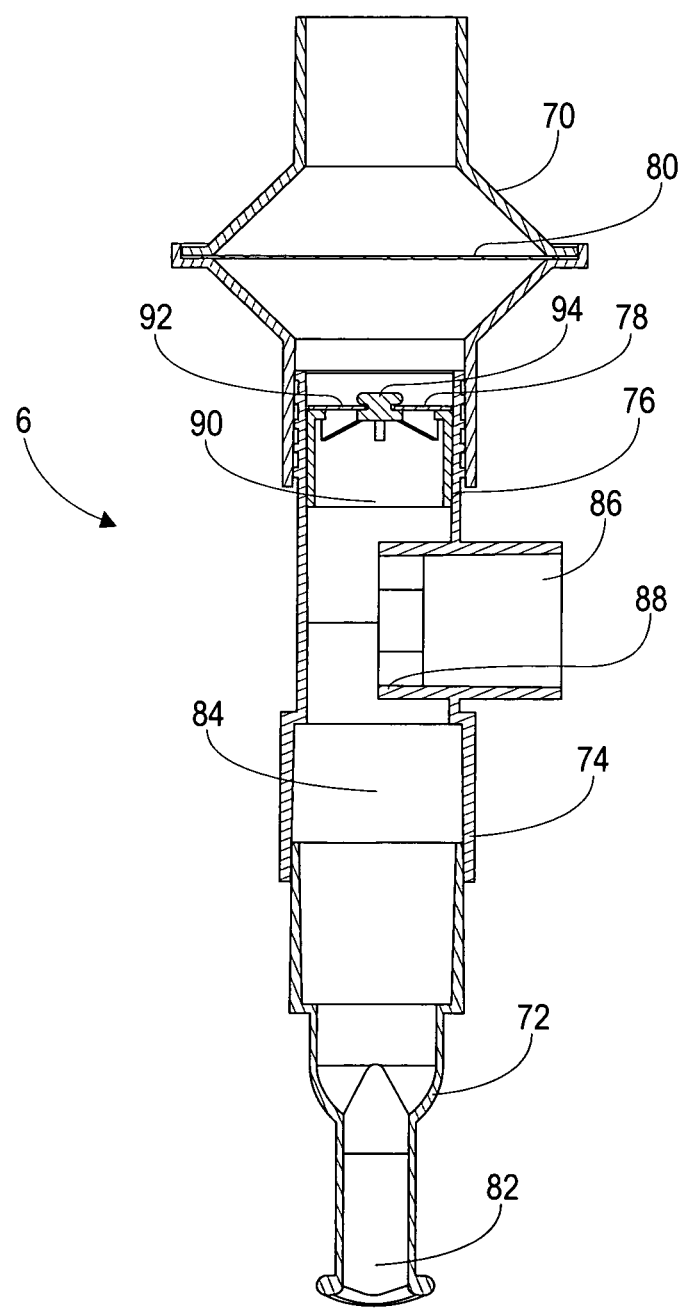
FIG. 15 is a sectional view of a patient tee assembly equipped with nebulizer tee, mouthpiece and exhalation filter.

Shield assembly 31 comprises impingement shield 32 shield yoke 33, shield flag 34 and yoke mounting flange 36 (FIG. 11). Impingement shield 32 is designed to at least partially prevent the movement of medicament nebula resulting from the interaction of the secondary shroud 24 and target surface 42 to aerosol chamber 16 when in at least one position, and to not prevent the movement of medicament nebula resulting form the interaction of secondary shroud 24 and target surface 42 to aerosol chamber 16 when in at least one other position. As depicted in the associated figures, a preferred embodiment of the impingement shield 32 is as a cylindrical ring having a height sufficient to at least partially occlude the fluid communication pathway and an interior diameter sufficient to circumscribe the outer diameter of a cylindrical cross-section region defined by the secondary shroud 24 and target surface 42. While the secondary shroud 24 target surface 42, and impingement shield 32 are depicted with circular cross-section, alternate cross-sectional geometries are possible so long as the impingement shield 32 can circumscribe the secondary shroud 24/target surface 42 and at least partially occlude the associated fluidic communication pathway with aerosol chamber 16.

Attached to impingement shield 32 is shield yoke 33. Shield yoke 33 connects the impingement shield 32 to a biasing support 40, and maintains the impingement shield 32 in proper orientation relative to the secondary shroud 24 and target surface 42. Shield yoke 33 may be connected to impingement shield 32 at one or more points and may be either a separate component durably affixed to impingement shield 32 or may be integrally formed with impingement shield 32. Shield yoke 33 terminates at yoke mounting flange 36.

Yoke mounting flange 36 is connected to shield yoke 33 at one or more points and may be either a separate component durably affixed to shield yoke 33 or may be integrally formed with shield yoke 33. Shield yoke may optionally include a shield flag 34. Shield flag 34 extends outside upper chamber 10, affording additional maintained orientation of the impingement shield 32 during operation of the nebulizer. In addition, shield flag 34 may be used to visually indicate operation of the nebulizer, or in the alternative, to trigger a simple and conventional logic circuit to electronically track operation of the nebulizer.

Within upper chamber 10, positioned in fluidic communication with aerosol chamber 16, is a durably affixed biasing support 40. Biasing support 40 is acted upon by respiration forces from the patient, wherein the force is translated into movement of the shield assembly 31. Suitable biasing support 40 includes membranes which are responsive to changes in force or flow of air through the nebulizer, and include elastomeric materials such silicone, natural rubbers and blocked AB polymers. Further, biasing support 40 may be homogenous in construction, or comprised of two or more differing materials, having regions of same or dissimilar cross-sectional profiles, and same or differing extension, recovery and related physical performance properties. Biasing support 40 may further include one or more biasing members, such as coil or leaf spring, to further act upon the shield assembly 31.

Aerosol chamber 16 consists of the space immediately around the aerosol producing region defined generally as the region between and including target surface 42 and the face of secondary shroud 24 coincident with the exit plane of entrainment orifice 26. Although in the preferred embodiment aerosol chamber 16 is encompassed by the internal geometry of insert 8, the invention need not be limited to said configuration and other embodiments in which the outer limits of aerosol chamber 16 are defined by the internal geometry of upper chamber 10 and/or lower chamber 12 are possible without departing from the invention.

At a point in upper chamber 10, proximal to biasing support 40 and on a side opposite to biasing support 40 that is in continuous fluid communication with aerosol chamber 16 is air inlet portal 44. Air inlet portal 44 provides fluid communication between the ambient environment and the interior of upper chamber 10. Ambient chamber 52 consists of the volume of space that is in un-interrupted flow communication of air inlet portal 44 and is in interrupted flow communication with aerosol chamber 16. Said interruption of flow communication between ambient chamber 52 and aerosol chamber 16 is caused by position of biasing support 40 such that during patient exhalation ambient chamber 52 and aerosol chamber are not in fluid communication, and fluid communication between ambient chamber 52 and aerosol chamber 16 only occurs in such instance that biasing support 40 has moved sufficient distance, either through force of inhalation or manual actuation, to allow impingement shield 32 sufficient movement so as to allow the movement of medicament nebula resulting from the interaction of the secondary shroud 24 and target surface 42 to aerosol chamber 16. Thus a useful feature of the invention is that the minimum amount of air needed to be drawn by the patient for the impingement shield 32 to be in a non-occluding position is only the gas flow caused to flow through jet orifice 30 since no ambient air may be drawn through the nebulizer until such time that ambient chamber 52 and aerosol chamber 16 are in fluid communication In a preferred embodiment, upper chamber 10 includes cylindrical guide 54, shield assembly 31 includes shield cam 56, shield flow ports 58, shield minimum flow channel 62, and shield flow diverter 64, and adjustment knob 60 includes adjustment knob actuation teeth 66. Cylindrical guide 54 extends axially and centrally into the internal space of upper chamber 10 such that it encompasses shield cam 56 and shield minimum flow channel 62. Adjustment knob actuation teeth 66 of adjustment knob 60 engage with shield cam 56 of shield assembly 31 such that rotation of adjustment knob 60 to the breath actuation mode allows for the travel of shield assembly up and down vertically with exhalation and inhalation of patient as herein described. Alternatively adjustment knob 60 may be rotated to the continuous mode, causing a different engagement of adjustment knob actuation teeth 66 with shield cam 56 such that shield assembly 31 is restricted to a down position so as to allow the movement of medicament nebula resulting from the interaction of the secondary shroud 24 and target surface 42 to aerosol chamber 16 regardless if the patient is inhaling or exhaling. Shield minimum flow channel 62 is located at the lowest point of shield cam 56. Upon initiation of patient inhalation ambient air is not allowed to pass from ambient chamber 52 to aerosol chamber 16 due to the impediment of fluid communication caused by the position of shield minimum flow channel 62 with respect to cylindrical guide 54. Upon patient inhalation becoming developed sufficiently to over-draw compressed gas provided through jet orifice 30, shield assembly 31 will travel downwards allowing movement of medicament nebula resulting from the interaction of secondary shroud 24 and target surface 42 to aerosol chamber 16, and causing shield minimum flow channel 62 to also travel downwards sufficiently to clear cylindrical guide 54 so as to create a gap between shield minimum flow channel 62 and cylindrical guide 54 and thereby forming intermittent ambient gas passage 68 and thus allowing the travel of ambient air through air inlet portal 44, ambient chamber 52, intermittent ambient gas passage 68, shield flow ports 58 and aerosol chamber 16. Upon patient exhalation, biasing support 40 is already in a position such that shield minimum flow channel 62 is in a position in relation to cylindrical guide 54 such that intermittent ambient gas passage 68 is not formed and thus exhaled gas is not allowed to escape out of or through nebulizer unit 4. Furthermore, with greater exhalation effort biasing support 40 is pushed with greater force upon cylindrical guide 54 creating a greater seal and impediment to exhaled flow. Thus an optimum embodiment of the invention includes the use of a mouthpiece, mask, or endotracheal tube unit or assembly that is equipped with a route for the passage of exhalation gases, and more optimally equipped with a route for the passage of exhalation gases that is biased in favor of exhalation gases flowing from the patient to the ambient environment during exhalation and biased against the flow of ambient air to the patient during inhalation since this gas may be more readily and effectively provided through nebulizer unit 4. An even more optimum configuration would include a filter through which exhaled gas was caused to pass through thus capturing exhaled particles not desired in the ambient environment. Patient tee assembly 6 shown in FIGS. 13 through 16 is one such optimum embodiment and is hereafter described in detail. Those skilled in the art can appreciate that a number of other configurations are possible that achieve the same objective of patient tee assembly 6, none of which depart from the present invention.

Further, without being constrained to specific theory, it is believed and understood by those skilled in the art that ambient air drawn through aerosol chamber 16 during inhalation allows for evaporation and reduction of size of droplets created by the aerosol producing region during patient inhalation, thus increasing the number of micro-droplets formed in the respirable range (i.e. 0-10 microns). The formation of copious of amounts of micro-droplets in the respirable range thereby forming an aerosol and filling out the remaining internal geometry of the invention and being drawn out by patient inhalation through aerosol outlet port 22 that is in fluid communication to the patient through use of a mouthpiece, mask, endotracheal tube or patient tee assembly 6.

If the inhalation triggered performance of nebulizer unit 4 is not desired, it is possible to override manually the impingement shield 32 through manual force applied to shield assembly 31, such as by applying downward force to optional shield flag 34. Force applied to shield flag 34 causes impingement shield 32 to move to the second, non-occluding position.

In general practice with the nebulizer unit 4 in accordance with the present invention, supplied gas to inlet port 20 at a pressure of at least 8 psig at a flow rate of between 1 and 15 liters of gas per minute, with the range of 5 to 12 liters per minute inclusively being preferred and the range of 8 to 11 liters per minute inclusively being most preferred. The gas issues through a jet orifice 30 having a diameter in the range of 0.011 and 0.030 inches. One or more liquid transfer conduits 28 are provided in secondary shroud 24 so that a volume of liquid medicament can be provided for aerosolization. The cross sectional flow area through which entrained liquid flows prior to entering aerosol producing area being 2 to 12 times greater than the cross sectional flow area of jet orifice 30. Impingement shield 32 having height at least as great as the distance from the exit plane of jet orifice 30 to the nearest point of target surface 42. Impingement shield 32 having an inside perimeter such that the minimum cross sectional area for the flow of gas from the nebulization area to the aerosol chamber 16 when impingement shield 32 is in the obstructing position has an equivalent diameter that is less than twenty times the equivalent diameter of jet orifice 30.

Figure 16:
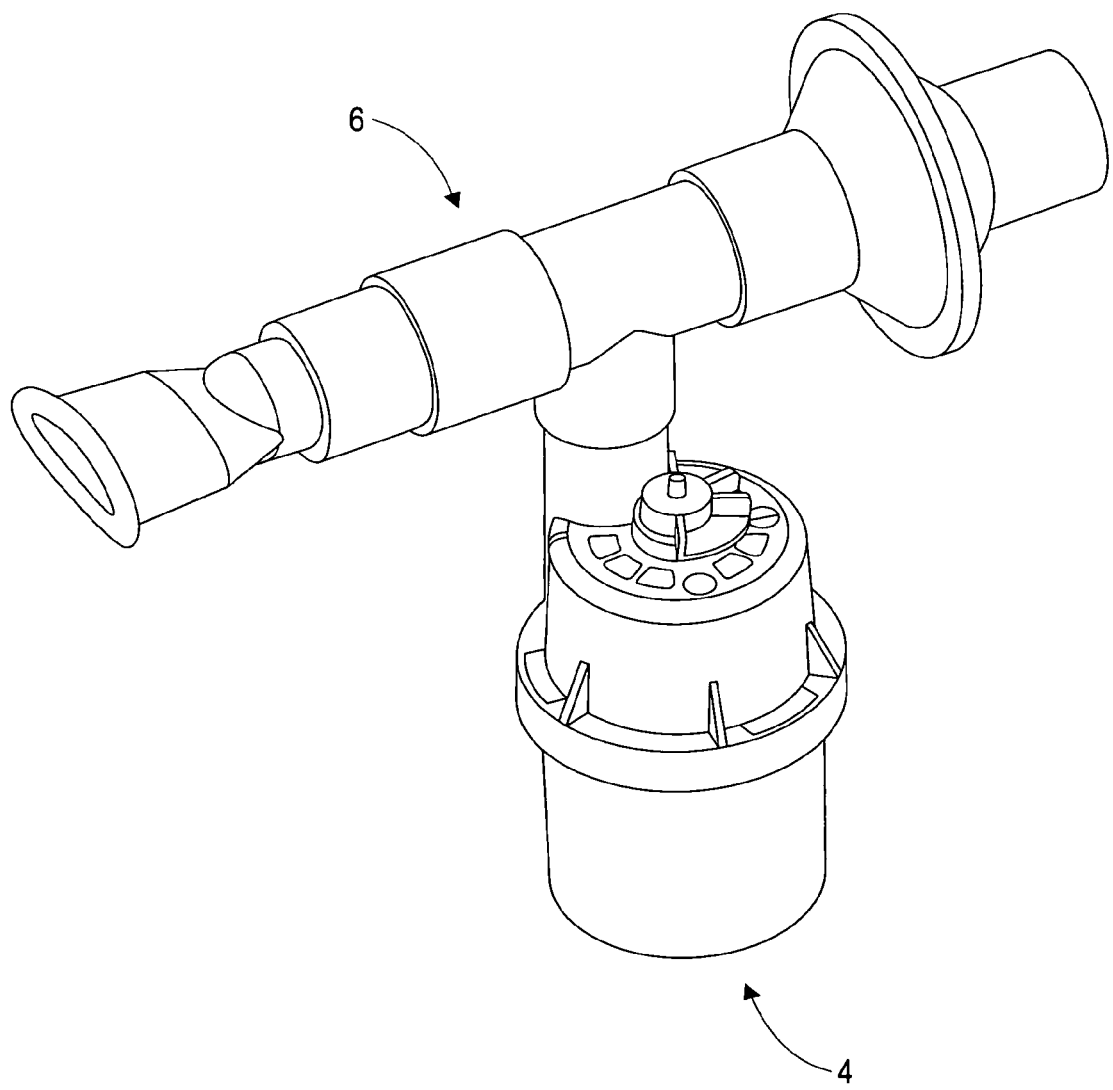
FIG. 16 is a perspective view of an inhalation controlled nebulizer fitted with a patient tee assembly.

It is within the purview of the present invention that an inhalation actuated nebulizer with impingement shield may be combined with one or more ancillary devices to further enhance respiratory therapy. A particularly advantageous embodiment includes use of a post nebulization filter, which upon a non-inhalation event, significantly reduces the release of residual medicament nebula from the nebulizer and patient. Such a post nebulization filter may operate by various modalities, including, but not limited to, size exclusion, impact, tortuous path, and depth filtration. Further, the post nebulization filter may include mechanically responsive means for cycling filter performance based on respiratory forces and recycling functions for returning captured medicament to the nebulizer liquid reservoir for reuse. Such combined nebulizer and post nebulizer filter(s) may be employed in situations where in the release of the medicament to the immediate atmosphere or ambient environment is expensive, deleterious to others, or of a controlled nature (i.e. palliative narcotics). One embodiment including said such post nebulizer filter configuration is shown in FIGS. 13-16 and is generally indicated by patient tee assembly 6. Post nebulization filter 70 is optional for patient tee assembly 6, which is an advantage of the demonstrated configuration of patient tee assembly 6 due to the additional expense of post nebulization filter 70 that is not needed in all instances. In addition to post nebulization filter 70, patient tee assembly 6 also consists of mouthpiece 72, nebulizer tee 74, check valve body 76, and check valve flapper 78. Post nebulization filter 70 includes filter membrane 80 that is positioned such that all gas passing through the body of post nebulization filter 70 is caused to pass through filter membrane 80. As known by those skilled in the art, filter membrane 80 may consist of a wide array of different materials depending on the expected need, including but not limited to glass fibers, cellulose acetate, cellulose nitrate, porous nylon and/or Teflon. Mouthpiece 72 includes a distal end shaped to comfortably fit in the patient's mouth and is equipped with a centrally positioned mouthpiece conduit 82 that allows gas to pass freely from either distal end to other. The distal end of mouthpiece 72 opposite the patient side is equipped with a tapered outside diameter, usually of 22 mm nominal dimension, and allows for press fit into mouthpiece port 84 of nebulizer tee 74. Nebulizer tee 74 also consists of nebulizer port 86, anti-drool chimney 88, and check valve port 90. Anti-drool chimney 88 is an internal feature to nebulizer tee 74 that is generally axially aligned with nebulizer port 86 but extends from the inside wall of nebulizer tee 74 towards the primary central axis sufficient distance that drool or bodily fluids excreted from the patients mouth that travel through mouthpiece conduit 82 are prevented from passing through nebulizer port 86 and into nebulizer unit 4 where they may be aerosolized and introduced to the patients lungs thus compromising the respiratory health of the patient. Nebulizer port 86 is a tapered diameter sized to engage with outer diameter of nebulizer outlet body 23. Check valve body 76 includes check valve flow conduits 92, and flapper retention boss 94. Check valve flapper 78 is made of an elastic material, such as silicone, and includes flapper retention orifice 96. When check valve flapper 78 is engaged with check valve body 76 by stretching check valve flapper 78 sufficiently for flapper retention orifice 96 to fit over flapper retention boss 94 the result is that check valve flapper 78 is held into place onto check valve body 76 so as to cover check valve flow conduits 92. Upon insertion of the resulting check valve assembly into check valve port 90, the result is a flow conduit that easily allows gas to pass out of nebulizer tee 74 through check valve port 90 and check valve flow conduits 92, but largely prevents the entrainment of gas in the opposite direction, thus when engaged with nebulizer unit 4, as shown in FIG. 16, exhaled gas is preferentially directed out of nebulizer tee 74 through check valve port 90. As herein described, nebulizer unit 4 is designed so that there is no route for exhaled gases to escape out of nebulizer unit 4, but that inhaled gas is preferentially drawn through nebulizer unit 4 as previously described and not check valve port 90. Upon placement of post nebulization filter 70 over check valve port 90, all exhaled gas is thereby caused to pass through post nebulizer filter 70 whereby undesired particles are captured on filter membrane 80 prior to exhaled gas being released to the ambient environment, thereby preventing contamination of the ambient environment with potentially undesirable aerosol which can lead to undesired exposure of additional people present at the time of treatment.

The general construction of functional elements of nebulizer unit 4 and patient tee assembly 6, includes thermoset and thermoplastic polymers as well as alloys and blends within those plastic families. Additional performance and aesthetic modifying chemistries can be incorporated during manufacture or after component or device fabrication. Of particular interest, polymers having specific surface energies can be used in different aspects of nebulizer unit 4 depending upon the degree of liquid medicament wet-out is desired. The nebulizer unit 4 and patient tee assembly 6 of the present invention is not constrained by the mode of manufacture and may include known or developed methods in molding and machining technology.

"Macro-droplets" are defined herein as being an individual unit of liquid medicament having an average diameter of greater than 10.0 micrometers and representing the predominant form of liquid medicament to pass through the aerosolization region and return to the reservoir. "Micro-droplets" are defined herein as being an individual unit of liquid medicament having an average diameter of less than or equal to 10.0 micrometers and being the predominant fraction of liquid medicament to pass through the aerosolization region and leave the nebulizer.

"Equivalent diameter" for any one or combination of cross sectional areas or conduits, of any shape, is defined herein as being the square root of the product of the cross sectional area, or sum of cross sectional areas for more than one cross sectional area or conduit, and four divided by Pi.

For the purposes of general background in aerosol technology and as indicia for the level of understanding resident in one skilled in the art of aerosol technology, the following references are incorporated by reference in their entireties as nonessential matter: "Aerosol Technology", Hinds, 1982 by Wiley and Sons, ISBN 0-471-087726-2; "Inhalation Aerosols", First Ed. Hickey, 1996 by Informa Healthcare, ISBN 0-8247-9702-7; and "The Mechanics of Aerosols", Fuchs et al., 1989 by Dover Publications, ISBN 0-486-66055-9.

EXAMPLE

A first embodiment nebulizer device in accordance with the present invention was fabricated and tested.

Device Dimensions:

| | |
|---|---|
| Nebulizer Unit height: | 3.75 inches |
| Nebulizer Unit width/diameter: | 1.88 inches |
| Shield Assembly Travel Distance: | 0.17 inches |
| Inhalation port dimensions: | 22 mm ISO ID "Respiratory Conduction Mouthpiece" |
| Liquid reservoir maximum volume fill: | 6.0 milliliters |
| Aerosol Outlet Port Diameter: | 0.90 inches |

In practice with the above example of a preferred embodiment, nebulizer unit 4 is supplied gas to inlet port 20 at a pressure of at least 8 psig, and more preferably at least 13 psig, at a flow rate of between 1 and 15 liters of gas per minute, with the range of 5 to 12 liters per minute inclusively being preferred and the range of 8 to 11 liters per minute inclusively being most preferred. The gas issues through a jet orifice having a diameter in the range of 0.011 to 0.030 inches, and more preferably in the range of 0.019 to 0.026 inches. The ratio of the cross sectional area that the liquid flows from into the aerosol producing region versus the cross sectional area of the jet orifice being preferably between 2 and 12 and more preferably between 4 and 8. The ratio of the distance from the exit plane of jet orifice to target surface and the diameter of entrainment orifice being preferably in the range of 0.1 and 0.8, and being more preferably in the range of 0.4 and 0.6. The ratio of the diameter of target surface and the entrainment orifice being preferably at least 1.0 and being more preferably at least 1.4. The height of impingement shield being preferably at least as large as the distance from the exit plane of the jet orifice to the nearest point of the target surface and being so positioned during exhalation or non-use to cause a redirection gas emanating from the target surface and jet orifice. The equivalent inside diameter of the minimum cross sectional area through which gas needs to flow from the nebulization area to the aerosol chamber as a result of the position of the impingement shield during exhalation or non-use being preferably less than the twenty times the equivalent diameter of the jet orifice, and being more preferably less than ten times the equivalent diameter of the jet orifice. When operating in the above format, it is possible to complete a 3 ml dosage of liquid medicament in less than four minutes of inhalation time at a nominal flow rate of 8 to 10 liters per minute under conditions in which aerosol is only delivered to the patient during inhalation, and by which viscous or thick medications can be delivered efficiently.

Testing

Inhalation Effort Evaluation Protocol a. Obtain a Competitive Commercial Model w/ Movable Baffle Technology (e.g. AeroEclipse Nebulizer by Trudell Medical International) and a representative example of the present invention as disclosed herein.
b. Place 3 ml of water into the nebulizer.
c. Connect to a Harvard pump (Model #).
d. Run at specified flow rate of 8 l/min.
e. Keep the inhalation ("I") to exhalation ("E") ratio at 1:1.
f. Adjust the tidal volume to 250 ml.
g. Start at a respiratory rate of 20 breaths per minute, and adjust the respiratory rate down until the AeroEclipse fails to produce aerosol during inhalation due to insufficient inhalation pressure.
h. Replace the AeroEclipse with an example in accordance with the present invention that incorporates an inhalation optimization feature as described.
i. Note whether any aerosol is being produced at the same settings and repeat the test.

Inhalation Effort Results

At a tidal volume of 250 ml, and an I:E ratio of 1:1, the AeroEclipse nebulizer stopped producing aerosol at a breathing rate of 12 breaths per minute (bpm) or less. Looking into the nebulizer it was visually determined that the moving critical component was not closing sufficient distance to allow aerosolization. The nebulizer in accordance with the present invention, including inhalation optimization feature, produced aerosol at 12 bpm, and continued to produce aerosol during inhalation at the same tidal volume and I:E ratio down to a breathing rate of 5 bpm.

Surface Tension Evaluation Protocol a. Obtain a Competitive Commercial Model w/ Movable Baffle Technology (e.g.

AeroEclipse Nebulizer by Trudell Medical International) and a representative example of the present invention as disclosed herein.

b. Mix albumin protein into water at 120 mg/ml.
c. Place 5 ml of protein mixture into AeroEclipse.
d. Connect nebulizer to a simulated patient condition of TV=425 ml, Respiratory Rate=16 bpm, and I:E=1:1.
e. Note if aerosol stops production during exhalation.
f. Repeat using an example in accordance with the present invention.

Surface Tension Results

When filled with 5 ml of albumin protein (120 mg/ml) the AeroEclipse nebulizer produced clearly visible aerosol during both inhalation and exhalation (indicative of breath-actuation mode failure). The nebulizer in accordance with the present invention, filled with 5 ml of albumin protein (120 mg/ml), cycled between aerosol production during inhalation and a proper cessation in aerosol production during simulated exhalation.

Adhesion Performance Degradation Evaluation Protocol a. Obtain a Competitive Commercial Model w/ Movable Baffle Technology (e.g. AeroEclipse Nebulizer by Trudell Medical International) and a representative example of the present invention as disclosed herein.
b. Mix acetylcysteine at 10 mg/ml in water (same concentration as recommended for the brand name equivalent Mucomyst)
c. Place 8 ml of acetylcysteine in AeroEclipse nebulizer.
d. Connect nebulizer to a simulated patient condition of TV=425 ml, Respiratory Rate=16 bpm, and I:E=1:1.
e. Using an aerosol trap on an inhalation limb to capture aerosolized medication delivered during inhalation.
f. Obtain an initial weight on nebulizer to determine gross output over the first minute.
g. Perform prescribed performance test for the first minute.

h. Run the nebulizer for 8 minutes.
i. Repeat the performance tests for another minute.
j. Compare the ratio of inhalation to gross output for the first minute to the last minute.
k. Repeat with example in accordance with the present invention.
l. Repeat for both devices using distilled water as a control test.

Adhesion Performance Degradation Results

When filled with 8 ml of Acetylcysteine 10 mg/ml (Mucomyst) and run over a total time of 8 minutes, the Aero-Eclipse showed a 25% reduction in the amount of medication delivered in the last minute as compared to the amount of medication delivered in the first minute. The shield nebulizer equivalent showed no significant drop in performance under the same conditions and during the same time period. Neither device showed any reduction in output when testing was repeated using distilled water.

Although the description above contains many details, these should not be construed as limiting the scope of the invention but as merely providing illustrations of some of the presently preferred embodiments of this invention. Therefore, it will be appreciated that the scope of the present invention fully encompasses other embodiments, which may become obvious to those skilled in the art. In the appended claims, reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the disclosure and present claims. Moreover, it is not necessary for a device or method to address every problem sought to be solved by the present invention, for it to be encompassed by the disclosure and present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A nebulizer comprising:
   a. an internal volume comprising an upper chamber and a lower chamber;
   b. an inhalation port in fluid communication with said internal volume and providing means for conduction of aerosol and gas from said internal volume to a patient;
   c. an liquid reservoir within said lower chamber;
   d. a gas inlet port adapted to receive pressurized gas and deliver it to said internal volume;
   e. a ejection nozzle in fluid communication with both of said gas inlet port and said liquid reservoir and which produces a medicament nebula when pressurized gas and liquid medicament are provided;
   f. an impingement shield which is capable of oscillating from a first position to a second position proximal to said ejection nozzle;
   wherein said impingement shield in said first position allows said medicament nebula to impact upon said impingement shield so that an increased fraction of the liquid medicament returns to said liquid reservoir in said lower chamber;
   Wherein said impingement shield in said second position allows an increased fraction of said medicament nebula of aerosolized liquid medicament into said upper chamber;
   Whereupon respiration by said patient causes said impingement shield to oscillate from said first position during a non-inhalation event to said second position during an inhalation event.

2. A nebulizer as in claim 1, wherein said impingement shield further comprises a biasing support.

3. A nebulizer as in claim 2, wherein said biasing support further comprises means for controlling air conduction through the nebulizer.

4. A nebulizer as in claim 3, wherein said means for controlling air conduction comprises an air inlet portal.

5. A nebulizer as in claim 1, wherein said ejection nozzle produces a medicament nebula by drawing liquid medicament into a pressurized gas stream.

6. A nebulizer as in claim 1, wherein said ejection nozzle produces a medicament nebula by drawing liquid medicament into a pressurized gas stream to form a liquid entrained jet, wherein said liquid entrained jet is impacted upon a target surface.

7. A nebulizer as in claim 1, wherein said impingement shield further comprises a flag.

8. A nebulizer as in claim 7, wherein said flag activates an electronic means for tracking nebulizer performance.

9. A nebulizer comprising of:
   a. an internal volume having therein an air chimney and an inhalation port for conduction of a gaseous suspension of aerosolized medicament to a respiring patient;
   b. a gas input port adapted to receive pressurized gas, extending from the outside the internal volume to the inside of the internal volume;
   c. a liquid reservoir;
   d. a ejection nozzle having a spray orifice in fluid communication with said gas inlet port and with said liquid reservoir, wherein said liquid reservoir communicates liquid medicament from the reservoir to the spray orifice by way of a liquid transfer conduit;
   e. an impingement shield which is capable of oscillating from a first position to a second position proximal to said ejection nozzle;
   wherein application of pressurized gas to said gas input port causes liquid medicament to move from the liquid reservoir and to mix into said pressurized gas to form a liquid entrained medicament nebula;
   wherein said impingement shield in said first position allows for said medicament nebula to impact upon said impingement shield forming macro-droplets of liquid medicament of which an increased fraction of said macro-droplets then return to said liquid reservoir in said lower chamber;
   wherein said impingement shield in said second position allows for said medicament nebula of liquid medicament of which an increased fraction of said medicament nebula are conveyed to said patient through said inhalation port;
   Whereupon respiration by said patient causes said oscillating baffle to oscillate from said first position during a non-inhalation event to said second position during an inhalation event.

10. A nebulizer as in claim 9, wherein said impingement shield further comprises a biasing support.

11. A nebulizer as in claim 10, wherein said biasing support further comprises means for controlling air conduction through the nebulizer.

12. A nebulizer as in claim 11, wherein said means for controlling air conduction comprises an air inlet portal.

13. A nebulizer as in claim 9, wherein said ejection nozzle produces a medicament nebula by drawing liquid medicament into a pressurized gas stream.

14. A nebulizer as in claim 9, wherein said ejection nozzle produces a medicament nebula by drawing liquid medicament into a pressurized gas stream to form a liquid entrained jet, wherein said liquid entrained jet is impacted upon a target surface.

15. A nebulizer as in claim 9, wherein said impingement shield further comprises a flag.

16. A nebulizer as in claim 15, wherein said flag activates an electronic means for tracking nebulizer performance.

17. A nebulizer as in claim 9, wherein said macro droplets are greater than about 10 micrometers in diameter.

18. A nebulizer as in claim 9, wherein said medicament nebula comprises micro droplets equal to or less than about 10 micrometers in diameter.

19. A nebulizer as in claim 9, wherein said ejection nozzle has a spray orifice of between 0.01 and 0.10 inch.

\* \* \* \* \*